US006355830B1

(12) United States Patent
Sakano et al.

(10) Patent No.: US 6,355,830 B1
(45) Date of Patent: Mar. 12, 2002

(54) PROCESS FOR PREPARATION OF DICARBOXYLIC ACID MONOESTERS

(75) Inventors: Kunihiko Sakano; Junji Fujii; Tetsuya Ikemoto, all of Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/269,765

(22) PCT Filed: Oct. 14, 1997

(86) PCT No.: PCT/JP97/03682

§ 371 Date: Apr. 9, 1999

§ 102(e) Date: Apr. 9, 1999

(87) PCT Pub. No.: WO98/16495

PCT Pub. Date: Apr. 23, 1998

(30) Foreign Application Priority Data

Oct. 15, 1996 (JP) .............................................. 8-272682

(51) Int. Cl.[7] .............................................. C07C 67/03
(52) U.S. Cl. ......................... 560/190; 560/92; 560/217
(58) Field of Search ........................... 560/92, 76, 190, 560/127, 217

(56) References Cited

U.S. PATENT DOCUMENTS

| 3,714,234 A | | 1/1973 | White | |
| 3,843,697 A | * | 10/1974 | Khaidukov et al. | 554/170 |
| 3,896,159 A | * | 7/1975 | Kratzer et al. | 560/78 |
| 4,082,788 A | * | 4/1978 | Mims | 558/443 |
| 4,314,071 A | * | 2/1982 | Babler | 560/127 |
| 4,559,180 A | * | 12/1985 | Green | 558/277 |
| 4,585,889 A | * | 4/1986 | Lentz et al. | 560/90 |
| 4,714,565 A | * | 12/1987 | Wevers et al. | 510/321 |

FOREIGN PATENT DOCUMENTS

| EP | 0 118 639 | 9/1984 |
| EP | 0 373 949 | 6/1990 |
| JP | 4-112854 | 4/1992 |
| JP | 4-182452 | 6/1992 |

OTHER PUBLICATIONS

Dieter Rehn, et al., J. Chem. Research (S), and J. Chem. Research (M), vol. 5, p. 119, and pp. 1501–1506 "Isocyanides As Activating Reagents For Carboxylic Acids; Ester Syntheses Under Mild Conditions", 1977.

George Bashiardes, et al., Journal of Organometallic Chemistry, vol. 364, No. 3, pp C29–C32, " Asymmetric Synthesis of Differentially Protected α–Alkyl Succinates", 1989.
Claudio J. Salomon, et al., Tetrahedron Letters, vol. 32, No. 34, pp. 4239–4242, " Bis (Tributyltin) Oxide. A Mild, Neutral and Selective Reagent for Cleavage of Esters. Scope and Limitation of the Reaction", 1991.
A. Paul Krapcho, et al., Tetrahedron Letters, No. 32, pp. 2721–2723, α–Carbalkoxylations of Carboxylic Acids. A General Synthetic Route to Monoesters of Malonic Acids., 1974.
B. Rigo, et al., Tetrahedron Letters, vol. 30, No. 23, pp. 3073–3076, " Reaction of Trimethylsilyl Derivatives with Meldrum's Acid: A New and Easy Monofunctionalization of Malonic Acid" 1989.
Fiziol. Akt. Veshchestva, vol. 7, pp. 129–131, " Monoesterification of Dicarboxylic Acids", 1975.
Eiji Ozaki, et al., Chemistry Letters, No. 7, pp. 539–540, "Enzymatic Preparation of Alkanedicarboxylic Acid Monoesters", 1995.
Takeshi Shimizu, et al., Synlett, No. 6, pp. 650–652,"Synthesis of Dicarboxylic Monoesters with Cyclic Anhydrides Under High Pressure", 1995.
Robert L. Augustine, et al., The Journal of Organic Chemistry, vol. 33, No.2, pp. 838–840, Self–Condensation of α–Keto Esters Under Stobbe Condensation Conditions[1].
Marie–Joelle De Vos, et al., Journal of the American Chemical Society, vol. 104, No. 15, pp. 4282–4283, "New Synthetic Route to (1R)–Trans–Chrysanthemic Ester and to the (1R)–CIS–Gem–Dibromovinyl Analogue from a Common Intermediate", Jul. 28, 1992.
Shimomura, et al., Journal of the Chemical Society, XP 002121737, Reaction ID 277427, Abstract only.
Shimomura, et al., Journal of the Chemical Society, XP 002121738, Reaction ID 201923, Abstract only.

* cited by examiner

*Primary Examiner*—Paul J. Killos
*Assistant Examiner*—Taylor V. Oh
(74) *Attorney, Agent, or Firm*—Oblon, Spivak, McClelland, Maier & Neustadt, P.C.

(57) ABSTRACT

A process for producing a dicarboxylic acid monoester which comprises subjecting a dicarboxylic acid monoester or an alkali metal salt of a dicarboxylic acid monoester and a metal alkoxide to transesterification in the presence of an organic solvent, or a process for producing a dicarboxylic acid monoester which comprises subjecting a dicarboxylic acid monoester or an alkali metal salt of a dicarboxylic acid monoester and an alcohol to transesterification in the presence of a metal alkoxide.

4 Claims, No Drawings

PROCESS FOR PREPARATION OF DICARBOXYLIC ACID MONOESTERS

TECHNICAL FIELD

The present invention relates to a process for producing dicarboxylic acid monoesters by transesterification of a dicarboxylic acid monoester which are useful as intermediates for medicines and agricultural chemicals, main starting materials for polyester polyols, nylons, fibers, lubricants, plasticizers, etc., or additives thereto or precursors thereof, especially useful as starting materials for synthesis of asymmetrical diesters of dicarboxylic acids.

BACKGROUND ART

Transesterifications using catalysts containing tin, titanium, etc. are well known, but these catalysts are deactivated if acids are present in the reaction systems. Therefore, these catalysts cannot be used for substrates containing carboxylic acid in the structure, such as dicarboxylic acid monoesters.

Under the circumstances, many processes for the production of dicarboxylic acid monoesters have been proposed, and these are roughly classified into the following five processes.
(a) Monoesterification of dicarboxylic acids:
   Fiziol. Akt. Veshchestva, 7, 129–31(1975).
   J. Chem. Res. Synopses, (5), 119(1977). JP-A-4-112854
(b) Decomposition of dicarboxylic acid diesters:
   Tetrahedron Lett., 32(34), 4239–42(1991).
   Chem. Lett., (7), 539–40(1995).
(c) Ring opening of cyclic dicarboxylic acid anhydrides with alcohols or metal alkoxides:
   Synlet, 6, 650–2(1995).
(d) Condensation reaction:
   J. Org. Chem., 33(2), 838–40(1968).
   Tetrahedron Lett., (32), 2721–3(1974).
   J. Organomet. Chem., 364(3), C29–32(1989).
(e) Synthesis of malonic monoesters from Meldrum's acid:
   Tetrahedron Lett., 30(23), 3073–6(1989).
   However, these processes (a)–(e) all have the following problems.

In the process (a), both the two carboxyl groups are esterified to produce diesters as by-products, and in the process (b), both the ester groups are hydrolyzed to produce dicarboxylic acids as by-products. Therefore, according to these processes, it is difficult to obtain monoesters with a high selectivity, and thus it is difficult to industrially efficiently obtain the desired monoesters. In the process (c), the reaction is carried out under a high pressure and special pressure reaction vessels such as autoclave are needed, resulting in increase of production cost. Moreover, according to this process, two kinds of monoesters are produced at the same time, and, hence, it is difficult to obtain selectively a monoester with a carboxyl group of the desired position being monoesterified. Furthermore, according to this process, when optically active monoesters are obtained using optically active cyclic dicarboxylic acid anhydrides as a starting material, there is the possibility that optical purity of the monoesters greatly decreases. In the case of the processes (d) and (e), the kinds of dicarboxylic acid monoesters which can be synthesized are limited and it is difficult to apply these processes to the production of a wide variety of dicarboxylic acid monoesters.

For these reasons, a process for industrially producing a wide variety of dicarboxylic acid monoesters at a high selectivity has been desired. Moreover, a process for producing dicarboxylic acid monoesters using optically active starting materials without causing a great reduction in optical purity has also been desired.

In general, transesterification between esters and metal alkoxides is known. However, when a dicarboxylic acid monoester as a starting material for esters and a metal alkoxide are subjected to transesterification in an organic solvent, production of a metal salt of the dicarboxylic acid monoester takes place in preference to transesterification, and since the resulting metal salt is hardly soluble in the organic solvent, it is considered that the desired transesterification hardly proceeds. There is no report on actually performing such reaction.

DISCLOSURE OF INVENTION

The present inventors have found that contrary to the above conventional common knowledge, even if a metal salt of dicarboxylic acid monoester represented by the formula (1) is produced in the reaction system, the transesterification satisfactorily proceeds by selecting the reaction conditions.

The object of the present invention is to provide a process for producing dicarboxylic acid monoesters according to which a wide variety of dicarboxylic acid monoesters can be obtained at a high selectivity by substituting a desired alkoxy group for an alkoxy group of the ester moiety of dicarboxylic acid monoesters which can be synthesized by known processes, and, furthermore, and optically active dicarboxylic acid monoesters can be produced from optically active starting materials with less deterioration of optical purity.

As a result of an intensive research conducted by the present inventors in an attempt to attain the above object, it has been found that a wide variety of dicarboxylic acid monoesters can be obtained at a high selectivity by subjecting an alcohol and a dicarboxylic acid monoester or an alkali salt of a dicarboxylic acid monoester to transesterification in the presence of a metal alkoxide or by subjecting a metal alkoxide and a dicarboxylic acid monoester or an alkali metal salt of a dicarboxylic acid monoester to transesterification in the presence of an organic solvent. Thus, the present invention has been accomplished.

That is, the present invention relates to a process for producing a dicarboxylic acid monoester represented by the formula (3) which comprises subjecting a dicarboxylic acid monoester or an alkali metal salt of a dicarboxylic acid monoester represented by the formula (1) as a starting material and a metal alkoxide represented by the formula (2) to transesterification in the presence of an organic solvent:

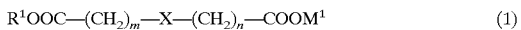

$$R^1OOC—(CH_2)_m—X—(CH_2)_n—COOM^1 \quad (1)$$

wherein $R^1$ represents a straight-chain or branched-chain alkyl group, alkoxyalkyl group or alkylthioalkyl group of 1–18 carbon atoms, of which one or more hydrogen atoms may be substituted with phenyl group, naphthyl group, toluyl group or fluorine atom, m and n each represent an integer of 0–12 (m+n≦18), X represents a group represented by one of the formula (X1) to the formula (X5), and $M^1$ represents a hydrogen atom or an alkali metal,

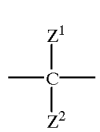

(X1)

in which $Z^1$ and $Z^2$ each represent a hydrogen atom, a fluorine atom, a phenyl group, a naphthyl group or a straight-chain or branched-chain alkyl group or alkenyl group of 1–12 carbon atoms,

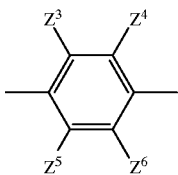
(X2)

in which $Z^3$, $Z^4$, $Z^5$ and $Z^6$ each represent a hydrogen atom, a fluorine atom, a chlorine atom or a bromine atom,

(X3)

in which $Z^1$ and $Z^2$ are as defined in the formula (X1),

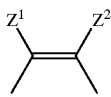
(X4)

in which $Z^1$ and $Z^2$ are as defined in the formula (X1),

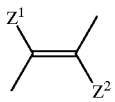
(X5)

in which $Z^1$ and $Z^2$ are as defined in the formula (X1);

$R^2OM^2$ (2)

wherein $R^2$ represents a straight-chain or branched-chain alkyl group, alkoxyalkyl group or alkylthioalkyl group of 1–18 carbon atoms, of which one or more hydrogen atoms may be substituted with phenyl group, naphthyl group, toluyl group or fluorine atom, and $M^2$ represents an alkali metal]; and $R^2OOC—(CH_2)_m—X—(CH_2)_n—COOM^1$ (3)

wherein $R^2$ is as defined in the formula (2), and m, n, X and $M^1$ are as defined in the formula (1).

Furthermore, the present invention relates to a process for producing a dicarboxylic acid monoester represented by the formula (5) which comprises subjecting a dicarboxylic acid monoester or an alkali metal salt of a dicarboxylic acid monoester represented by the formula (1) as a starting material and an alcohol represented by the formula (4) to transesterification in the presence of a metal alkoxide represented by the above formula (2):

$R^3OH$ (4)

wherein $R^3$ represents a straight-chain or branched-chain alkyl group, alkoxyalkyl group or alkylthioalkyl group of 1–18 carbon atoms, of which one or more hydrogen atoms may be substituted with phenyl group, naphthyl group, toluyl group or fluorine atom; and $R^3OOC—(CH_2)_m—X—(CH_2)_n—COOM^1$ (5)

wherein $R^3$ is as defined in the formula (4), and m, n, X and $M^1$ are as defined in the formula (1)

BEST MODE FOR CARRYING OUT THE INVENTION

The dicarboxylic acid monoesters or alkali metal salts of the dicarboxylic acid monoesters used as a starting material in the present invention are not limited as far as they are represented by the formula (1), and they may be those which are commercially available or synthesized by known processes. As these dicarboxylic acid monoesters or alkali metal salts of the dicarboxylic acid monoesters (hereinafter referred to as "starting monoesters"), mention may be made of, for example, monoesters of adipic acid, terephthalic acid, malonic acid, methylsuccinic acid, succinic acid, itaconic acid, citraconic acid, glutaric acid and the like, or metal salts of these monoesters. The metals which form the metal salts here are not limited as far as they are alkali metals, but potassium and sodium are preferred, and potassium is especially preferred because the salts formed are superior in solubility. Moreover, the starting monoesters may be optical active compounds.

The metal alkoxides used as a starting material of the transesterification in place of alcohol are not limited as far as they are represented by the formula (2), but potassium alkoxides are especially preferred because they are superior in solubility. The kind of the alkoxy group of the metal alkoxides depends on the desired dicarboxylic acid monoesters and is not particularly limited. Preferred are methoxy group, ethoxy group, n-propoxy group, n-butoxy group and tert-butoxy group. When the metal alkoxide is used as a starting material of the transesterification, the amount of the metal alkoxide may be 1.01 mol or more per mol of the starting dicarboxylic acid monoester (hereinafter sometimes referred to as "starting monoester"), and preferably 1.01–3 mols per mol of the starting mono-esters taking the cost into consideration. If the amount of the metal alkoxide is less than 1 mol per mol of the starting monoesters, an acid-base reaction takes place preferentially and this is not preferred.

The metal alkoxides to be allowed to exist in the reaction system when alcohol is used as a starting material of the transesterification in place of metal alkoxide are not limited as far as they are represented by the formula (2), but potassium alkoxides are especially preferred because they are superior in solubility. The kind of the alkoxy group of the metal alkoxides is not limited, but preferred are methoxy group, ethoxy group, n-propoxy group, n-butoxy group and tert-butoxy group. However, if the alkoxy group of the starting alcohol is different from that of the metal alkoxide, undesired esters are partially produced, and, hence, it is preferred to use a metal alkoxide having the same alkoxy group as of the alcohol represented by the formula (4) used in the reaction. When the metal alkoxide is used as a catalyst for the transesterification as mentioned above, the amount of the metal alkoxide may be 1.01 mol or more per mol of the starting monoester in the case of the starting monoesters being dicarboxylic acid monoester, and preferably 1.01–3 mols per mol of the starting monoester taking the cost into consideration. In the case of the starting monoesters being the alkali metal salt, the amount of the metal alkoxide may be 0.01 mol or more per mol of the starting monoester, and preferably 0.01–2 mols per mol of the starting monoester taking the cost into consideration.

The alcohols used as a starting material in the present invention are not limited as far as they are represented by the formula (4). Examples of these alcohols (hereinafter referred to as "starting alcohols") include straight-chain aliphatic alcohols such as methanol, ethanol, n-propyl alcohol and n-butyl alcohol, branched aliphatic alcohols such as isopropyl alcohol, isobutyl alcohol and tert-butyl alcohol, unsaturated aliphatic alcohols such as allyl alcohol and methallyl alcohol, alcohols containing aromatic group such as benzyl alcohol, 4-nitrobenzyl alcohol, 3,5-dinitrobenzyl alcohol and phenethyl alcohol, and cellosolve alcohols such as ethylene glycol monomethyl ether and diethylene glycol monomethyl ether.

The amount of the starting alcohol used is preferably 1–200 mols, especially preferably 5–50 mols per mol of the starting monoesters. When the starting monoesters are an alkali metal salt, it is preferred to use the starting alcohol in a greatly excess amount over the amount of the alkali metal salt of the starting monoester for the purposes of improving the solubility of the alkali metal salt as the starting monoester, shortening the reaction time and improving the conversion in the transesterification. However, in case the starting alcohol has a high boiling point and is difficult to remove by distillation after completion of the reaction or the amount of the starting alcohol should be decreased because of its high price, use of the starting alcohol in a slightly excess amount per mol of the starting monoesters can fully attain the purposes.

When an alcohol is used as a starting material and a metal alkoxide is used as a catalyst, the order of mixing of the starting materials before subjected to the reaction is not particularly limited, and, for example, there are the following methods: a method of mixing the starting monoesters with the alcohol which is another starting material and thereafter adding the metal alkoxide (method A); a method of mixing the starting alcohol with the metal alkoxide and thereafter adding the starting monoesters (method B); a method of mixing the starting monoesters with the metal alkoxide and thereafter adding the starting alcohol (method C); a method of mixing the starting monoesters with an organic solvent and an additive and thereafter adding the metal alkoxide (method D); a method of mixing the metal alkoxide with an organic solvent and an additive and thereafter adding the starting monoesters (method E); etc. The order of mixing according to methods A, B, D and E are preferred from the point of operability.

When the starting monoesters are optical active compounds having an asymmetric center at α-position, there is the possibility of α-hydrogen of the is ester being drawn by the metal alkoxide. Therefore, in order to maintain a high optical purity of the product, it is preferred to add the metal alkoxide lastly as in the method A or D.

When a starting alcohol is used in the present invention, the solvent and the additive are not necessarily needed, but they may be used for the acceleration of the reaction. When the starting alcohol is not used, a solvent is necessarily used and an additives) can be optionally added.

The solvents usable include organic solvents, for example, aromatic hydrocarbon solvents such as benzene, nitrobenzene, toluene and xylene, ether solvents such as tetrahydrofuran, 1,2-dimethoxyethane, 1,3-dioxolan and 1,4-dioxane, carbon disulfide, nitromethane, N,N-dimethylformamide, and dimethyl sulfoxide.

The additives are preferably those which activate the carbonyl group of the metal alkoxide or ester, those which have an effect of increasing the solubility of the metal alkoxide or the starting monoesters or those which have an effect as a phase-transfer catalyst. Examples of the additives include amines such as triethylamine and tetramethylenediamine, nitrogen-containing aromatic compounds such as pyridine, quaternary ammonium salts such as benzyltriethylammonium chloride and tetra-n-butylammonium bromide, crown ethers such as 18-crown-6, and compounds having an inclusion effect similar to that of the crown ethers, such as tetrahydrofuran, 1,2-dimethoxyethane, 1,3-dioxolan and 1,4-dioxane.

Reaction temperature of the transesterification can be optionally set usually in a range of −100 to 250° C., preferably −80 to 200° C., more preferably −20 to 150° C. Since the reaction of the present invention is an equilibrium reaction, in order to improve the reaction rate and the conversion, it is preferred to carry out the reaction while alcohol ($R^1OH$) produced from the starting monoesters by transesterification is removed out of the reaction system by evaporation, etc. Therefore, the reaction temperature is preferably not less than the boiling point or azeotropic point of the alcohol ($R^1OH$) produced by the transesterification. In case the alcohol resulting from the metal alkoxide used as a starting material or the starting alcohol is also simultaneously distilled off by evaporation, this alcohol or a solution containing this alcohol may be added to the reaction system.

The pressure during the transesterification can be optionally set usually in a range of 1 kPa–5 MPa (absolute pressure). Practically, 10 kPa–1 MPa (absolute pressure) is preferred, and 80–120 kPa (absolute pressure) is more preferred. The reaction time of the transesterification can be optionally set usually in a range of 0.01–100 hours, and 0.1–50 hours is preferred considering the efficiency of reaction vessel.

The present invention will be further specifically explained by the following examples and comparative examples, which should not be construed as limiting the present invention in any manner.

The analysis in the examples and comparative examples was conducted by gas chromatography (hereinafter referred to as "GC"), high-performance liquid chromatography (hereinafter referred to as "HPLC"), and NMR.

The purity of the final products was calculated by the following formula from peak area in a GC or HPLC chart.

$$\text{Purity}(\%) = A/B \times 100$$

wherein A denotes a peak area of the dicarboxylic acid monoester which is the desired product, and B denotes the total of peak areas of the desired product and all impurities.

Furthermore, yield was calculated by the following formula.

$$\text{Yield}(\%) = C/D \times 100$$

wherein C denotes the number of mols of the di-carboxylic acid monoester which is the desired product (calculated by dividing the product of the purity and the weight of the final product containing impurities by the molecular weight of the dicarboxylic acid monoester which is the desired product), and D denotes the number of mols of the starting monoesters.

EXAMPLE 1

Synthesis of mono-tert-butyl adipate

Ten grams (0.057 mol) of monoethyl adipate and 200 ml (2.081 mols) of tert-butyl alcohol were charged in a glass flask equipped with a stirrer, a dropping funnel, a thermometer, an Oldershaw column and a Dimroth condenser, and 7.73 g (0.069 mol, 1.2 equivalent) of potassium-tert-butoxide was poured thereinto little by little at room temperature. As a result, the reaction mixture generated heat to cause rising of the temperature to 35° C., and white crystals were precipitated in the reaction mixture. Thereafter, the reaction mixture was heated to 83° C. and the reaction was carried out for 16.5 hours, during which ethyl alcohol produced by the transesterification was distilled off together with tert-butyl alcohol, and tert-butyl alcohol in the same amount as the amount of the distilled tert-butyl alcohol was continuously added through the dropping funnel. After completion of the transesterification, tert-butyl alcohol was distilled off under normal pressure, and the residue was allowed to stand for cooling. Then, 80 ml of ice water was added to the residue, followed by separation washing twice with 100 ml of n-hexane. To the resulting aqueous phase was added 3.96 g (0.039 mol, 1.4 equivalent) of sulfuric acid diluted with 20 ml of cold water to liberate the acid. The components in the aqueous phase were analyzed by GC to obtain a peak area ratio of 20:80 of the starting monoethyl adipate and the product mono-tert-butyl adipate. This aqueous phase was subjected to extraction twice with 100 ml of n-hexane, and then the n-hexane phase extracted twice was washed thrice with 10 ml of pure water and thereafter subjected to concentration under reduced pressure. As a result, 7.20 g of mono-tert-butyl adipate of 92% in purity containing no monoethyl adipate was obtained. The yield in this case was 57%. Spectrum data of $^1$H-NMR on the product were as follows.

$^1$H-NMR(CDCl$_3$) 1.48 (9H, s), 1.64–1.68 (4H, m), 2.22–2.27 (2H, m), 2.33–2.40 (2H, m), 9.64 (1H, br).

EXAMPLE 2

Synthesis of mono-tert-butyl terephthalate

In the same manner as in Example 1, 10 g (0.056 mol) of monomethyl terephthalate and 200 ml (2.081 mols) of tert-butyl alcohol were charged, and 8.10 g (0.070 mol, 1.3 equivalent) of potassium-tert-butoxide was poured thereinto little by little at room temperature. As a result, the reaction mixture generated heat to result in rising of the temperature to 35° C., and white crystals were precipitated in the reaction mixture. Thereafter, the reaction mixture was heated to 83° C. and the reaction was carried out for 17 hours, during which methyl alcohol produced by the transesterification was distilled off together with tert-butyl alcohol, and tert-butyl alcohol in the same amount as the amount of the distilled tert-butyl alcohol was continuously added through the dropping funnel. After completion of the transesterification, tert-butyl alcohol was distilled off under normal pressure, and the residue was allowed to stand for cooling. Then, 80 ml of ice water was added to the residue, followed by separation washing twice with 100 ml of n-hexane. To the resulting aqueous phase was added 3.85 g (0.036 mol, 1.4 equivalent) of sulfuric acid diluted with 20 ml of cold water to liberate the acid. The components in the aqueous phase were analyzed by GC to obtain a peak area ratio of 66:34 of the starting monomethyl terephthalate and the product mono-tert-butyl terephthalate. This aqueous phase was subjected to extraction twice with 100 ml of n-hexane, and then the n-hexane phase extracted twice was washed thrice with 10 ml of pure water and thereafter subjected to concentration under reduced pressure. As a result, 2.99 g of mono-tert-butyl terephthalate of 94% in purity containing no monomethyl terephthalate was obtained. The yield in this case was 23%. Spectrum data of $^1$H-NMR on the product were as follows.

$^1$H-NMR(CDCl$_3$) 1.62 (9H, s), 8.08 (2H, d, J=8.1 Hz), 8.16 (2H, d, J=8.1 Hz).

EXAMPLE 3

Synthesis of monoisopropyl malonate

In the same manner as in Example 1, 5 g (0.029 mol) of potassium salt of monoethyl malonate and 100 ml (1.305 mol) of isopropyl alcohol were charged, and 0.41 g (0.0059 mol, 0.2 equivalent) of potassium methoxide was poured thereinto little by little at room temperature. As a result, the reaction mixture generated heat to result in rising of the temperature to 35° C., and white crystals were precipitated. Thereafter, the reaction mixture was heated to 82° C. and the reaction was carried out for 6 hours, during which ethyl alcohol produced by the transesterification was distilled off together with isopropyl alcohol, and isopropyl alcohol in the same amount as the amount of the distilled isopropyl alcohol was continuously added through the dropping funnel. After completion of the transesterification, isopropyl alcohol was distilled off under normal pressure, and the residue was allowed to stand for cooling. Then, 100 ml of ice water was added to the residue, followed by separation washing once with 100 ml of ethyl acetate. To the resulting aqueous phase was added 1N hydrochloric acid to adjust the pH to 2. The components in the aqueous phase was analyzed by HPLC to obtain a peak area ratio of 4:96 of monoethyl malonate resulting from the starting potassium salt of monoethyl malonate and the product monoisopropyl malonate. The analysis conditions by HPLC are shown below.

Analysis conditions for high-performance liquid chromatography:

Column: ODS-120A

Mobile phase: Water/acetonitrile/phosphoric acid= 20:80:0.1 (vol)

Flow rate: 0.7 ml/min

Detection: 220 nm

This aqueous phase was subjected to extraction twice with 100 ml of ethyl acetate, and then the ethyl acetate phase extracted twice was washed twice with 100 ml of pure water and thereafter subjected to concentration under reduced pressure. As a result, 4.03 g of monoisopropyl malonate of 95% in purity containing no monoethyl malonate was obtained. The yield in this case was 90%. Spectrum data of $^1$H-NMR on the product were as follows.

$^1$H-NMR (CDCl$_3$) 1.27 (6H, d, J=6.21 Hz), 3.40 (2H, s), 5.08 (1H, se, J=6.21 Hz), 9.53 (1H, br).

EXAMPLE 4

Synthesis of monobenzyl malonate

In the same manner as in Example 1, 10 g (0.059 mol) of potassium salt of monoethyl malonate and 200 ml (1.929 mol) of benzyl alcohol were charged, and 0.1 g (0.0001 mol, 0.02 equivalent) of potassium methoxide was poured thereinto little by little at room temperature. As a result, the reaction mixture generated heat to result in rising of the temperature to 35° C., and white crystals were precipitated. Thereafter, the reaction mixture was heated to 90° C. and the reaction was carried out for 6 hours, during which ethyl alcohol (containing a slight amount of methyl alcohol resulting from potassium methoxide) produced by the transesterification was continuously distilled off. After completion of the reaction, the reaction mixture was left to stand for cooling. Then, 100 ml of ice water was added thereto, followed by subjecting to separation washing once with 100 ml of ethyl acetate. To the resulting aqueous phase was added 1N hydrochloric acid to adjust the pH to 2. The components in the aqueous phase was analyzed by HPLC to find that monoethyl malonate resulting from the starting potassium salt of monoethyl malonate was not detected and only the product monobenzyl malonate was detected. The analysis conditions for HPLC were the same as in Example 3. This aqueous phase was subjected to extraction twice with 100 ml of ethyl acetate, and then the ethyl acetate phase extracted twice was washed twice with 100 ml of pure water and thereafter subjected to concentration under reduced pressure. As a result, 10.83 g of monobenzyl malonate of 100% in purity was obtained. The yield in this case was 95%. Spectrum data of $^1$H-NMR on the product were as follows.

$^1$H-NMR(CDCl$_3$) 3.41 (2H, s), 5.22 (2H, s), 7.37 (5H, s).

EXAMPLE 5

Synthesis of 4-tert-butyl itaconate

In the same manner as in Example 1, 1.44 g (0.013 mol, 1.2 equivalent) of potassium-tert-butoxide and 15 ml (0.156 mol) of tert-butyl alcohol were charged, and 1.5 g (0.010 mol) of 4-methyl itaconate was poured thereinto little by little at room temperature. As a result, the reaction mixture generated heat to result in rising of the temperature to 35° C., and white crystals were precipitated. Thereafter, the reaction mixture was heated to 83° C. and the reaction was carried out for 7 hours, during which methyl alcohol produced by the transesterification was distilled off together with tert-butyl alcohol, and tert-butyl alcohol in the same amount as the amount of the distilled tert-butyl alcohol was continuously added through the dropping funnel. After completion of the transesterification, tert-butyl alcohol was distilled off under normal pressure, and the residue was allowed to stand for cooling. Then, 26 ml of ice water was added to the residue, followed by separation washing once with 30 ml of n-hexane. To the resulting aqueous phase was added 0.74 g (0.07 mol, 1.4 equivalent) of sulfuric acid diluted with 4 ml of cold water to liberate the acid. The components in the aqueous phase were analyzed by GC to find that the peak area ratio of the starting 4-methyl itaconate and the product 4-tert-butyl itaconate was 61:39. This aqueous phase was subjected to extraction twice with 30 ml of n-hexane, and then the n-hexane phase extracted twice was washed once with 3 ml of pure water and thereafter subjected to concentration under reduced pressure. As a result, 0.54 g of 4-tert-butyl itaconate of 88% in purity containing no 4-methyl itaconate was obtained. The yield in this case was 24%. Spectrum data of $^1$H-NMR on the product were as follows.

$^1$H-NMR(CDCl$_3$) 1.45 (9H, s), 3.26 (2H, s), 5.78 (1H, s), 6.42 (1H, s), 8.05 (1H, br).

EXAMPLE 6

Synthesis of 4-benzyl (R)-methylsuccinate

In the same manner as in Example 1, 4.67 g (0.082 mol, 1.2 equivalent) of potassium methoxide and 150 ml (1.447 mol) of benzyl alcohol were charged, and 10 g (0.060 mol) of 88% by weight of 4-methyl (R)-methylsuccinate (optical purity: 94%e.e.) was added dropwise thereto over a period of 5 minutes at room temperature. As a result, the reaction mixture generated heat to result in rising of the temperature to 35° C., and white crystals were precipitated. Thereafter, the reaction mixture was heated to 100° C. and the reaction was carried out for 5 hours, during which methyl alcohol produced by the transesterification and a slight amount of methyl alcohol resulting from potassium methoxide were continuously distilled off. After completion of the reaction, the reaction mixture was allowed to stand for cooling. Then, 100 ml of ice water was added thereto, followed by separation washing once with 100 ml of ethyl acetate. To the resulting aqueous phase was added 4.94 g (0.048 mol, 1.4 equivalent) of sulfuric acid diluted with 25 ml of cold water to liberate the acid. The components in the aqueous phase were analyzed by GC to find that the peak area ratio of the starting 4-methyl (R)-methylsuccinate and the product 4-benzyl (R)-methylsuccinate was 17:83. This aqueous phase was subjected to extraction twice with 100 ml of ethyl acetate, and then the ethyl acetate phase extracted twice was washed once with 20 ml of pure water and thereafter subjected to concentration under reduced pressure. As a result, 7.87 g of 4-benzyl (R)-methylsuccinate of 87% in purity was obtained. The yield in this case was 51%. The 4-benzyl (R)-methylsuccinate had an optical purity of 94% e.e., and no reduction of optical purity relative to the starting methyl ester was seen. The Spectrum data of $^1$H-NMR on the product were as follows.

$^1$H-NMR(CDCl$_3$) 1.25 (3H, d, J=6.8 Hz), 2.42 (2H, dd, J=12.7, 5.9 Hz), 2.74 (2H, dd, J=12.7, 8.4 Hz), 2.96 (1H, dtd, J=8.4, 6.8, 5.9 Hz), 5.13 (2H, s), 7.35 (5H, s), 10.74 (1H, br).

The optical purity was obtained by analysis using HPLC with converting the starting 4-benzyl (R)-methyl-succinate to (R)-methylsuccinic acid with 2 equivalents of aqueous sodium hydroxide solution. The analysis conditions for HPLC are shown below.

Column: CHIRALCEL OD

Mobile phase: n-hexane/isopropyl alcohol/trifluoroacetic acid=90:10:0.1(vol)

Flow rate: 0.5 ml/min

Detection: 220 nm

The starting 4-methyl (R)-methylsuccinate was prepared by the process disclosed in JP-A-8-285.

EXAMPLE 7

Synthesis of 4-tert-butyl (R)-methylsuccinate 142.5 g (1.231 mols, 1.2 equivalent) of potassium-tert-butoxide and 1500 ml (5.202 mols) of tert-butyl alcohol were charged in a glass flask equipped with a stirrer, a dropping funnel, a thermometer, an Oldershaw column and a Dimroth condenser, and 150 g (0.904 mol) of 88% by weight of 4-methyl (R)-methylsuccinate (optical purity: 94%e.e.) was added dropwise thereto at room temperature over a period of 5 minutes. As a result, the reaction mixture generated heat to result in rising of the temperature to 35° C., and white crystals were precipitated. Thereafter, the reaction mixture was heated to 83° C. and the reaction was carried out for 26 hours, during which methyl alcohol produced by the transesterification was distilled off together with tert-butyl alcohol, and tert-butyl alcohol in the same amount as the amount of the distilled tert-butyl alcohol was continuously added through the dropping funnel. After completion of the transesterification, tert-butyl alcohol was distilled off under normal pressure, and the residue was allowed to stand for cooling. Then, 1100 ml of ice water was added to the residue, followed by separation washing once with 1000 ml of n-hexane. To the resulting aqueous phase was added 75.6 g (0.74 mol, 1.4 equivalent) of sulfuric acid diluted with 400 ml of cold water to liberate the acid. The components in the aqueous phase were analyzed by GC to obtain a molar ratio of 25:75 (75% in terms of conversion) of the starting 4-methyl (R)-methylsuccinate and the product 4-tert-butyl (R)-methylsuccinate. This aqueous phase was subjected to extraction twice with 1500 ml of n-hexane, and then the n-hexane phase extracted twice was washed thrice with 300 ml of pure water and thereafter subjected to concentration under reduced pressure. As a result, 100.9 g of 4-tert-butyl (R)-methylsuccinate of 92.0% in purity containing no 4-methyl (R)-methylsuccinate was obtained. The yield in this case was 58%. The optical purity of 4-tert-butyl (R)-methylsuccinate was 92%e.e., and reduction of the optical purity relative to the starting methyl ester was slight. Spectrum data of $^1$H-NMR on the product were as follows.

$^1$H-NMR(CDCl$_3$) 1.24 (3H, d, J=6.8 Hz), 1.44 (9H, s), 2.36 (2H, dd, J=16.3, 6.1 Hz), 2.64 (2H, dd, J=16.3, 8.1 Hz), 2.90 (1H, dtd, J=8.1, 6.8, 6.1 Hz), 9.73 (1H, br).

The optical purity of the starting 4-methyl (R)-methylsuccinate and that of the product 4-tert-butyl (R)- methylsuccinate were obtained by analysis using HPLC with converting them to (R)-methylsuccinic acid with 2 equivalents of aqueous sodium hydroxide solution and with a greatly excess amount of trifluoroacetic acid, respectively. The analysis conditions for HPLC were the same as in Example 6.

EXAMPLE 8

Synthesis of 4-tert-butyl (R)-methylsuccinate

In the same manner as in Example 7, 10 g (0.066 mol) of 97% by weight of 4-methyl (R)-methylsuccinate (optical purity: 99%e.e.) and 100 ml (1.040 mols) of tert-butyl alcohol were charged, and 9.5 g (0.082 mol, 1.2 equivalent) of potassium-tert-butoxide was added dropwise thereto at room temperature over a period of 5 minutes. As a result, the reaction mixture generated heat to result in rising of the temperature to 35° C., and white crystals were precipitated. Thereafter, the reaction mixture was heated to 83° C. and the reaction was carried out for 15.5 hours, during which methyl alcohol produced by the transesterification was not distilled off. After completion of the transesterification, the produced methyl alcohol and tert-butyl alcohol were distilled off under reduced pressure, and the residue was allowed to stand for cooling. Then, 75 ml of ice water was added to the residue, followed by separation washing once with 100 ml of n-hexane. To the resulting aqueous phase was added 4.75 g (0.046 mol, 1.4 equivalent)of sulfuric acid diluted with 25 ml of cold water to liberate the acid. The components in the aqueous phase were analyzed by GC to obtain a molar ratio of 65:35 (35% in terms of conversion) of the starting 4-methyl (R)-methylsuccinate and the product 4-tert-butyl (R)-methylsuccinate. This aqueous phase was subjected to extraction twice with 100 ml of n-hexane, and then the n-hexane phase extracted twice was washed six times with 20 ml of pure water and thereafter subjected to concentration under reduced pressure. As a result, 3.76 g of 4-tert-butyl (R)-methylsuccinate of 99% in purity containing no 4-methyl (R)-methylsuccinate was obtained. The yield in this case was 30%. The optical purity of 4-tert-butyl (R)-methylsuccinate was 99%e.e., and no reduction of the optical purity relative to the starting methyl ester was seen. Spectrum data of $^1$H-NMR on the product were the same as in Example 7. The optical purity was measured in the same manner as in Example 7.

EXAMPLE 9

Synthesis of 4-tert-butyl (R)-methylsuccinate

In the same manner as in Example 7, 158.3 g (1.369 mol, 2.0 equivalents) of potassium-tert-butoxide and 1000 ml (10.404 mols) of tert-butyl alcohol were charged, and 100 g (0.664 mol) of 97% by weight of 4-methyl (R)-methylsuccinate (optical purity: 99%e.e.) was added dropwise thereto at room temperature over a period of 5 minutes. As a result, the reaction mixture generated heat to result in rising of the temperature to 35° C., and white crystals were precipitated. Thereafter, the reaction mixture was heated to 83° C. and the reaction was carried out for 30 minutes, during which methyl alcohol produced by the transesterification was not distilled off. After completion of the transesterification, methyl alcohol produced and tert-butyl alcohol were distilled off under reduced pressure, and the residue was allowed to stand for cooling. Then, 1000 ml of ice water was added to the residue, followed by separation washing once with 1000 ml of n-hexane. To the resulting aqueous phase was added 171.3 g (1.643 mols, 1.4 equivalent) of concentrated hydrochloric acid to liberate the acid. The components in the aqueous phase were analyzed by GC to obtain a molar ratio of 20:80 (80% in terms of conversion) of the starting 4-methyl (R)-methylsuccinate and the product 4-tert-butyl (R)-methylsuccinate. This aqueous phase was subjected to extraction twice with 1000 ml of n-hexane, and then the n-hexane phase extracted twice was washed thrice with 100 ml of pure water and thereafter subjected to concentration under reduced pressure. As a result, 89.54 g of 4-tert-butyl (R)-methylsuccinate of 99% in purity containing no 4-methyl (R)-methylsuccinate was obtained. The yield in this case was 71%. The optical purity of 4-tert-butyl (R)-methylsuccinate was 94%e.e., and reduction of the optical purity relative to the starting methyl ester was slight. Spectrum data of $^1$H-NMR on the product were the same as in Example 7. The optical purity was measured in the same manner as in Example 7.

EXAMPLE 10

Synthesis of 4-tert-butyl (R)-methylsuccinate

In the same manner as in Example 7, 103.0 g (1.050 mol, 1.2 equivalent) of sodium tert-butoxide and 1450 ml (15.085 mols) of tert-butyl alcohol were charged, and 145.2 g (0.875 mol) of 88% by weight of 4-methyl (R)-methylsuccinate (optical purity: 94%e.e.) was added dropwise thereto at room temperature over a period of 5 minutes. As a result, the reaction mixture generated heat to result in rising of the temperature to 35° C., and white crystals were precipitated in the reaction mixture. Thereafter, the reaction mixture was heated to 83° C. and the reaction was carried out for 3 hours, during which methyl alcohol produced by the transesterification was distilled off together with tert-butyl alcohol, and tert-butyl alcohol in the same amount as the distilled tert-butyl alcohol was continuously added through the dropping funnel. After completion of the transesterification, methyl alcohol produced and tert-butyl alcohol were distilled off under reduced pressure, and the residue was allowed to stand for cooling. Then, 1095 ml of ice water was added to the residue, followed by separation washing once with 1000 ml of n-hexane. To the resulting aqueous phase was added 71.0 g (0.695 mol, 1.4 equivalents) of sulfuric acid diluted with 355 ml of cold water to liberate the acid. The components in the aqueous phase were analyzed by GC to obtain a molar ratio of 70:30 (30% in terms of conversion) of the starting 4-methyl (R)-methylsuccinate and the product 4-tert-butyl (R)-methylsuccinate. This aqueous phase was subjected to extraction twice with 1450 ml of n-hexane, and then the n-hexane phase extracted twice was washed six times with 290 ml of pure water and thereafter subjected to concentration under reduced pressure. As a result, 30.8 g of 4-tert-butyl (R)-methylsuccinate of 99% in purity containing no 4-methyl (R)-methylsuccinate was obtained. The yield in this case was 19%. The optical purity of 4-tert-butyl (R)-methylsuccinate was 94%e.e., and no reduction of the optical purity than the starting methyl ester was seen. Spectrum data of $^1$H-NMR on the product were the same as in Example 7. The optical purity was measured in the same manner as in Example 7.

EXAMPLE 11

Synthesis of 4-tert-butyl (R)-methylsuccinate

A metal tert-butoxide an additive and a solvent were charged, and 4-methyl (R)-methylsuccinate was added dropwise thereto at 0° C. or room temperature over a period of 5 minutes. As a result, white crystals were precipitated in the reaction mixture. After completion of the transesterification, 30% cold sulfuric acid (1.4 equivalents) was added to liberate the acid. This aqueous phase was subjected to extraction twice with n-hexane, and then the n-hexane phase extracted twice was washed five times with pure water and thereafter subjected to concentration under reduced pressure. As a result, 4-tert-butyl (R)-methylsuccinate of higher than 90% in purity containing no 4-methyl (R)-methylsuccinate was obtained. The yield in this case was as shown in Table 1. Spectrum data of $^1$H-NMR on the products were the same as in Example 7. The optical purity was measured in the same manner as in Example 7.

40%. The optical purity of 4-tert-butyl (R)-methylsuccinate was 84%e.e., and a great reduction of the optical purity relative to the starting methylsuccinic anhydride was seen. The optical purity was measured in the same manner as in Example 7, regarding both the 4-ester and the 1-ester as (R)-methylsuccinic acid.

TABLE 1

| | Reaction conditions | | | | Optical | |
|---|---|---|---|---|---|---|
| t-BuOM (equivalent) Additive (equivalent) | Amount of solvent (ml/g) based on reaction scale | Temperature of bath | Reaction time | Yield/% | purity/% ee (Optical purity of substrate) | Reaction scale |
| t-BuOK (3.0) | t-BuOH (10) | rt | 30 min | 39.2 | 97 (98) | 20 g |
| t-BuOK (2.2) | DMSO (5) | rt | 16.5 h | 4.0 | 92 (98) | 20 g |
| t-BuOK (2.2) | dioxane (7.5) | rt | 30 min | 27.8 | 93 (97) | 200 g |
| t-BuOK (2.2) | dioxolane (7.5) | rt | 1 h | 28.5 | 95 (97) | 200 g |
| t-BuONa (2) | DME (20) | rt | 16 h | 39.1 | 87 (94) | 10 g |
| t-BuONa (2.2) | DME (7.5) | rt | 30 min | 28.2 | 93 (97) | 200 g |
| t-BuOK (2.2) | DME (7.5) | rt | 30 min | 32.0 | 94 (97) | 200 g |
| t-BuONa (2.2) | THF (5) | 0° C. | 2 h | 35.7 | 86 (94) | 20 g |
| t-BuOK (2.2) | THF (10) | rt | 4.5 h | 30.9 | 90 (98) | 20 g |
| t-BuOK (3) | THF (5) | 0° C. | 30 min | 37.4 | 96 (98) | 20 g |
| t-BuOK (2.2) | THF (7.5) | rt | 30 min | 29.9 | 91 (97) | 200 g |
| t-BuOK (2.2) | THF (7.5) DMSO (2.5) | rt | 30 min | 24.5 | 96 (97) | 200 g |
| t-BuOK (2.2) pyridine (2.3) | THF (7.5) | rt | 30 min | 35.8 | 94 (97) | 200 g |
| t-BuOK (2.2) Et$_3$N (2.3) | THF (7.5) | rt | 30 min | 33.1 | 92 (97) | 200 g |
| t-BuOK (2.2) TMEDA (1.2) | THF (7.5) | rt | 30 min | 25.9 | 93 (97) | 20 g |
| t-BuOK (2.2) PhCH$_2$NEt$_3$.Cl (0.2) | THF (7.5) | 0° C. | 1 h | 37.3 | 93 (97) | 200 g |
| t-BuOK (2.2) PhCH$_2$NEt$_3$.Cl (0.2) | THF (3.75)–t-BuOH (2.5) | 0° C. | 1 h | 41.2 | 96 (97) | 200 g |

(Note)
rt: Room temperature

Comparative Example 1

Synthesis of 4-tert-butyl (R)-methylsuccinate

In the same manner as in Example 9, 2.84 g (0.290 mol, 1.1 equivalents) of sodium tert-butoxide and 30 ml (0.312 mol) of tert-butyl alcohol were charged, and 3.0 g (0.260 mol) of 99% by weight of (R)-methylsuccinic anhydride (optical purity: 96%e.e. or more) suspended in 30 ml (0.312 mol) of tert-butyl alcohol was added dropwise thereto at room temperature over a period of 5 minutes. As a result, the reaction mixture generated heat to result in rising of the temperature to 54° C., and at this temperature, the reaction was carried out for 30 minutes. After completion of the transesterification, tert-butyl alcohol was distilled off under reduced pressure, and the residue was allowed to stand for cooling. Then, 200 ml of ice water was added to the residue, followed by separation washing once with 200 ml of ethyl acetate. To the resulting aqueous phase was added 2.93 g (0.290 mol, 1.1 equivalents) of concentrated hydrochloric acid to liberate the acid. This aqueous phase was subjected to extraction thrice with 200 ml of n-hexane, and then the n-hexane phase extracted thrice was washed once with 60 ml of pure water and thereafter subjected to concentration under reduced pressure. As a result, 2.0 g of a mixture of 4-tert-butyl (R)-methylsuccinate and 1-tert-butyl (R)-methylsuccinate containing no 4-methyl (R)-methylsuccinate was obtained. This mixture was analyzed by GC to obtain a molar ratio of position isomers of 4-ester:1-ester=70:30, and when these two components were combined, the purity was 99%. The yield in this case was

INDUSTRIAL APPLICABILITY

According to the present invention, a wide variety of dicarboxylic acid monoesters can be obtained at a high selectivity, and especially when optically active esters represented by the formula (1) having an asymmetric center at a-position of carboxylic acid are used as starting materials, substantially no reduction of optical purity is seen before and after the reaction. Therefore, according to the present invention, there are obtained dicarboxylic acid monoesters which are useful as intermediates for medicines and agricultural chemicals, main starting materials or additives for polyester polyols, nylons, fibers, lubricants, plasticizers, etc., or precursors thereof, especially useful as starting materials for synthesis of asymmetrical diesters of dicarboxylic acids.

What is claimed is:

1. A process for producing a dicarboxylic acid monoester represented by the formula (3) which comprises subjecting a dicarboxylic acid monoester or an alkali metal salt of a dicarboxylic acid monoester represented by the formula (1) as a starting material and a metal alkoxide represented by the formula (2) to transesterification in the presence of an organic solvent:

$$R^1OOC-(CH_2)_m-X-(CH_2)_n-COOM^1 \qquad (1)$$

wherein $R^1$ represents a straight-chain or branched-chain alkyl group, alkoxyalkyl group or alkylthioalkyl group of 1–18 carbon atoms, of which one or more hydrogen atoms may be substituted with phenyl group, naphthyl group, toluyl group or fluorine atom, m and n each represent an integer of 0–12 ($m+n \leq 18$), X represents a group represented by one of the formula (X1) to the formula (X5), and $M^1$ represents a hydrogen atom or an alkali metal, (X1)

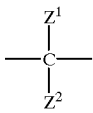

in which $Z^1$ and $Z^2$ each represent a hydrogen atom, a fluorine atom, a phenyl group, a naphthyl group or a straight-chain or branched-chain alkyl group or alkenyl group of 1–12 carbon atoms, (X2)

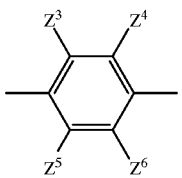

in which $Z^3$, $Z^4$, $Z^5$ and $Z^6$ each represent a hydrogen atom, a fluorine atom, a chlorine atom or a bromine atom, (X3)

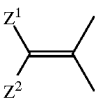

in which $Z^1$ and $Z^2$ are as defined in the formula (X1), (X4)

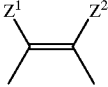

in which $Z^1$ and $Z^2$ are as defined in the formula (X1), (X5)

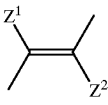

in which $Z^1$ and $Z^2$ are as defined in the formula (X1);

$$R^2OM^2 \qquad (2)$$

wherein $R^2$ represents a straight-chain or branched-chain alkyl group, alkoxyalkyl group or alkylthioalkyl group of 1–18 carbon atoms, of which one or more hydrogen atoms may be substituted with phenyl group, naphthyl group, toluyl group or fluorine atom, and $M^2$ represents an alkali metal; and $$R^2OOC-(CH_2)_m-X-(CH_2)_n-COOM^1 \qquad (3)$$

wherein $R^2$ is as defined in the formula (2), and m, n, X and $M^1$ are as defined in the formula (1).

2. A process according to claim 1, wherein the transesterification is carried out in the presence of a quaternary ammonium salt or a tertiary amine.

3. A process for producing a dicarboxylic acid monoester represented by the formula (5) which comprises subjecting an optically active dicarboxylic acid monoester or an alkali metal salt of a dicarboxylic acid monoester represented by the formula (1) as a starting material and an alcohol represented by the formula (4) to transesterification in the presence of a metal alkoxide represented by the formula (2):

$$R^1OOC-(CH_2)_m-X-(CH_2)_n-COOM^1 \qquad (1)$$

wherein $R^1$ represents a straight-chain or branched-chain alkyl group, alkoxyalkyl group or alkylthioalkyl group of 1–18 carbon atoms, of which one or more hydrogen atoms may be substituted with phenyl group, naphthyl group, toluyl group or fluorine atom, m and n each represent an integer of 0–12 (m+n≦18), X represents a group represented by one of the formula (X1) to the formula (X5), and $M^1$ represents a hydrogen atom or an alkali metal, (X1)

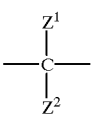

in which $Z^1$ and $Z^2$ each represent a hydrogen atom, a fluorine atom, a phenyl group, a naphthyl group or a straight-chain or branched-chain alkyl group or alkenyl group of 1–12 carbon atoms, (X2)

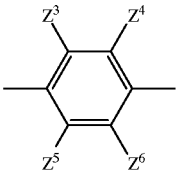
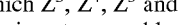

in which $Z^3$, $Z^4$, $Z^5$ and $Z^6$ each represent a hydrogen atom, a fluorine atom, a chlorine atom or a bromine atom, (X3)

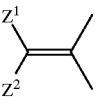

in which $Z^1$ and $Z^2$ are as defined in the formula (X1), (X4)

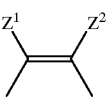

in which $Z^1$ and $Z^2$ are as defined in the formula (X1), (X5)

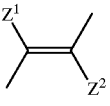

in which $Z^1$ and $Z^2$ are as defined in the formula (X1);

$$R^2OM^2 \qquad (2)$$

wherein $R^2$ represents a straight-chain or branched-chain alkyl group, alkoxyalkyl group or alkylthioalkyl group of 1–18 carbon atoms, of which one or more hydrogen atoms may be substituted with phenyl group, naphthyl group, toluyl group or fluorine atom, and $M^2$ represents an alkali metal;

$$R^3OH \qquad (4)$$

wherein $R^3$ represents a straight-chain or branched-chain alkyl group, alkoxyalkyl group or alkylthioalkyl group of 1–18 carbon atoms, of which one or more hydrogen atoms may be substituted with phenyl group, naphthyl group, toluyl group or fluorine atom and $$R^3OOC-(CH_2)_m-X-(CH_2)_n-COOM^1 \qquad (5)$$

wherein $R^3$ is as defined in the formula (4), and m, n, X and $M^1$ are as defined in the formula (1).

4. A process according to claim 3, wherein the transesterification is carried out in the presence of a quaternary ammonium salt or a tertiary amine.

\* \* \* \* \*